United States Patent [19]

Breitkopf et al.

[11] Patent Number: 4,918,247

[45] Date of Patent: Apr. 17, 1990

[54] PROCESS FOR THE PREPARATION OF 2,2-DIMETHYLPROPANEDIOL-1,3

[75] Inventors: Norbert Breitkopf; Wolfgang Hofs, both of Oberhausen; Heinz Kalbfell, Schermbeck; Franz Thonnessen, Oberhausen; Peter Lappe, Dinslaken; Helmut Springer, Oberhausen, all of Fed. Rep. of Germany

[73] Assignee: Ruhrchemie Aktiengesellschaft, Fed. Rep. of Germany

[21] Appl. No.: 361,711

[22] Filed: May 26, 1989

[30] Foreign Application Priority Data

Dec. 30, 1986 [DE] Fed. Rep. of Germany ....... 3644675

Related U.S. Application Data

[63] Continuation-in-part of Ser. No. 138,284 Dec. 24, 1987 abandoned.

[51] Int. Cl.[4] .................... C07C 29/14; C07C 29/38; C07C 31/20
[52] U.S. Cl. ..................................... 568/854; 568/853
[58] Field of Search ............................... 568/854, 853

[56] References Cited

U.S. PATENT DOCUMENTS

| | | | |
|---|---|---|---|
| 3,340,312 | 9/1967 | Duke et al. | 568/854 |
| 3,808,280 | 4/1974 | Merger et al. | 568/854 |
| 4,393,251 | 7/1983 | Broecker et al. | 568/811 |
| 4,594,461 | 6/1986 | Merger et al. | 568/853 |
| 4,740,639 | 4/1988 | Bearers | 568/853 |

FOREIGN PATENT DOCUMENTS

| | | |
|---|---|---|
| 1057083 | 5/1959 | Fed. Rep. of Germany . |
| 1518784 | 8/1969 | Fed. Rep. of Germany . |
| 1957591 | 5/1971 | Fed. Rep. of Germany . |

OTHER PUBLICATIONS

Chemical Abstract #34798P, American Chemical Society, Chemical Abstracts, vol. 73, No. 7, p. 282 (8/17/70).

Primary Examiner—J. E. Evans
Attorney, Agent, or Firm—Jordan B. Bierman

[57] ABSTRACT

Preparation of 2,2-dimethylpropanediol-1,3 by the aldol addition of isobutyraldehyde and formaldehyde using tri-n-propylamine as a catalyst, followed by hydrogenation of the reaction mixture, and subsequent distillation of the hydrogenation product in the presence of isobutanol and water.

13 Claims, No Drawings

PROCESS FOR THE PREPARATION OF 2,2-DIMETHYLPROPANEDIOL-1,3

This application is a continuation of application Ser. No. 138,284, filed Dec. 24, 1987 now abandoned.

The present invention relates to a process for the preparation of 2,2-dimethylpropanediol-1,3 from isobutyraldehyde and formaldehyde using tri-n-propylamine as a catalyst, followed by hydrogenation of the reaction mixture, and subsequent distillation of the hydrogenation product in the presence of isobutanol and water.

It is known that 2,2-dimethyl-3-hydroxypropanal can be prepared from isobutyraldehyde and formaldehyde by aldol addition and the oxyaldehyde subsequently hydrogenated to the corresponding diol. Alkaline-reacting compounds find application as catalysts for the aldol addition; the use of alkali hydroxides, alkaline earth hydroxides and alkali carbonates being widespread for this purpose. In addition, amines—especially tertiary mono or polyamines, e.g. diamines—are suitable. Such a process is, for example, described in DE 19 57 591 B2.

In order to prepare 2,2-dimethylpropanediol-1,3, isobutyraldehyde and formaldehyde are reacted in the presence of tertiary amines and the reaction mixture obtained is hydrogenated. Among others, the following may be used; trimethyl, triethyl, methyldiethyl, methyldiisopropyl, and tributylamines. In the examples, only triethylamine is used as a catalyst.

The use of amines as addition catalysts has the advantage that by-products, which are formed when other alkaline catalysts are used, are not produced. However, the disadvantage is that tertiary amines are expensive reagents and, therefore, for the process to be cost-effective, the amine from the reaction mixture must be recovered with, if possible, no losses. A quantitative separation of the amines is also necessary because diol contaminated with even only minimal amounts of amine is unsuitable for many applications. Therefore, the preparation of pure 2,2-dimethylpropanediol-1,3 requires a highly complicated separation.

Hence, it is an object of the invention to develop a process which is technically simple to perform and permits the recovery of 2,2-dimethylpropanediol-1,3 by amine-catalyzed aldol addition in an economically feasible manner.

The present invention comprises a process for the preparation of 2,2-dimethylpropanediol-1,3 by the addition of isobutyraldehyde and formaldehyde in the presence of tertiary amines as catalysts, followed by hydrogenation of the reaction mixture, and subsequent distillation of the hydrogenation product, wherein tri-n-propylamine is used as a catalyst and distillation takes place in the presence of isobutanol.

The new process provides very pure 2,2-dimethylpropanediol-1,3, which no longer contains even traces of amine. A further advantage of the procedure according to the invention is the slight loss of amine throughout all the reaction steps. Of the original amount of amine used, as much as 97 wt. % of this expensive material is recovered. The unexpected advantage of the process are due to the excellent suitability of tri-n-propylamine as an addition catalyst coupled with the use of isobutanol as a solvent and part of the reaction medium, preferably in every step of the process. In addition, the formation of various azeotropes containing two or all three of tri-n-propylamine, isobutanol, and water, contribute to the efficiency of the process. Their formation ensures complete separation, not only of the tri-n-propylamine as the highest-boiling component, but also of the other components, as well as providing low thermal loading of the reaction product. The fact that the amine is recycled and can be re-used as a catalyst is another advantage of the new process which deserves special mention.

In the course of the multi-step process, tri-n-propylamine is present in the reaction mixture from the very beginning. The same applies to the water, as formaldehyde is normally used as an aqueous solution. Isobutanol can also be added to the original reaction mixture; however, it is also possible to perform the addition reaction with excess isobutyraldehyde or in the presence of an isobutyraldehyde/isobutanol mixture. During the hydrogenation following the addition reaction, isobutanol is then formed from the aldehyde. Finally, isobutanol can also be added to the hydrogenation product before its distillation. The amount of isobutyraldehyde or isobutanol is measured so that the ratio of isobutanol to the remaining feed material (in parts by weight) in the distillation stage is 1:40 to 1:200, preferably 1:80 to 1:100.

In the first reaction stage, formaldehyde and isobutyraldehyde are reacted with each other. While they can be reacted in molar ratio, it is also possible to use one of the two reagents in excess. It is expedient to use formaldehyde as an aqueous solution (aldehyde content: 37 wt. %). The reaction takes place at temperatures between 20° and 100° C.; preferably 80° to 95° C. In general, the reaction is carried out at normal pressure but elevated pressure can also be used. Apart from water from the formaldehyde solution and any isobutanol added, no other solvents are necessary. Tri-n-propylamine is used as a catalyst and is contained in the reaction mixture in an amount of 1 to 20, preferably 2 to 12, mol % based on the isobutyraldehyde.

The reaction is advantageously carried out in an agitator-equipped vessel, or in a reaction tube which is charged with packing material to improve the mixing of the reagents. The reaction takes place exothermally and can be accelerated by heating. The reaction mixture formed is catalytically hydrogenated, without separation into its components or removal of any individual components. The addition of hydrogen can take place in the gaseous phase or in the liquid phase. Nickel carrier catalysts, which may, if desired, contain further active metals such as copper or chromium and activators, are particularly suitable.

The hydrogenation product is fed into a continuously operating fractionating column with 40 to 120, preferably 50 to 70, plates. The column is operated with two side outlets, the temperature of hydrogenation product used and the amount of distillate withdrawn being adjusted with respect to each other so that 2,2-dimethylpropanediol 1,3 with a purity of at least 99% is left in the bottom of the column. At the lower side outlet, tri-n-propylamine and residual amounts of isobutanol are withdrawn and, at the upper side outlet, a two-phase system is removed, the organic phase of which consists primarily of isobutanol. At the head of the column, methanol is formed which is removed together with low-boiling by-products. The reaction water and the remaining methanol are separated via the aqueous phase of the upper side outlet.

The new procedure is characterized by the simplicity of its engineering and its economy. These advantages are due to the fact that the feed material is worked up in two distillation stages. Since the isobutanol phase obtained at the upper side outlet is recycled to the feed of the column, the system is impoverished of water through the formation of the azeotrope isobutanol/$H_2O$ (boiling point 90° C. and containing 33% $H_2O$). Therefore, tri-n-propylamine can be removed at the lower side outlet although tri-n-propylamine forms a binary azeotrope boiling point (97° C. and containing 44.3% $H_2O$) and also a ternary azeotrope (boiling point 91° C. and containing 50% isobutanol, 19% tri-n-propylamine, and 31% $H_2O$). Depending on the water content of the feed material and its composition, the amount of recycled butanol must be dosed so that the entire amount of water is obtained at the upper side outlet.

The new process is explained in more detail by the following examples, which are intended to illustrate the invention.

EXAMPLE 1

A reaction mixture comprising 56% by weight 2,2-dimethylpropanediol-1,3; 20% by weight isobutanol; 13% by weight water; 7% by weight tri-n-propylamine; 3% by weight methanol; and 1% by weight other components is subjected to continuous distillation. The distillation column has a total of 60 theoretical plates, a stripping section of 10 plates and a rectifying section of 50 plates. There are side outlets at the 20th and 40th plates. The desired 2,2-dimethylpropanediol-1,3 is recovered as bottoms and has a purity of more than 90%.

Most of the methanol is withdrawn from the head of the column, the overhead containing approximately 85% by weight methanol, the remainder being first running components; namely, isobutanol and water.

The ratio of feed to recycled isobutanol is 100 to 70 and isobutanol and water are obtained at the upper side outlet and 97% of the amine having a purity of 90% is drawn off at the lower side outlet. The amine can be recycled to the aldolization reaction without further purification.

EXAMPLE 2

The process was carried out in accordance with Example 1 except that the ratio of feed mixture to recycled butanol is 100:30. In this case, only incomplete separation of the components tri-n-propylamine, isobutanol and water is achieved.

EXAMPLE 3 (Comparative Example)

A reaction mixture containing 47.6% by weight 2,2-dimethylpropanediol-1,3; 33.3% by weight isobutanol; 12.4% by weight water; 4.8% by weight triethylamine; and 1.9% by weight methanol is distilled in a column having 70 theoretical plates and one side outlet. The process is otherwise the same as that of Example 1.

Even with a recycling ratio of greater than 100:1 and a removal of distillate from the column head of only 1%, sufficient separation of methanol and triethylamine cannot be obtained.

Moreover, the fact that triethylamine has good water solubility is a disadvantage; the entire amount withdrawn at the side outlet—both the organic and aqueous phases—must be recycled to the aldolization reaction, since the amine is to be found in both.

We claim:

1. A process for the preparation of 2,2-dimethyl-propanediol-1,3 comprising reacting isobutyraldehyde with an aqueous solution of formaldehyde in the presence of tri-n-propylamine to form a reaction mixture, hydrogenating said mixture to produce a hydrogenation product, and distilling said hydrogenation product in the presence of isobutanol to obtain highly pure 2,2-dimethyl-propanediol-1,3 wherein the weight ratio of said isobutanol to said hydrogenation product is from 1:40 to 1:200.

2. The process of claim 1 wherein there is 1 to 20 mol % of said amine present based on said isobutyraldehyde.

3. The process of claim 2 wherein there is 2 to 12 mole % of said amine present based on said isobutyraldehyde.

4. The process of claim 1 wherein said ratio is from 1:80 to 1:100.

5. The process of claim 1 wherein said reaction takes place in the presence of isobutanol.

6. The process of claim 1 wherein said reaction is carried out at a temperature of 20° to 100° C.

7. The process of claim 6 wherein said temperature is 80° to 95° C.

8. The process of claim 1 wherein the ratio of said distillate to said product is adjusted to yield said diol having a purity of at least 99%.

9. The process of claim 1 wherein said distillation yields an isobutanol phase which is recycled to said distillation.

10. The process of claim 1 wherein said amine is recycled in said reaction.

11. The process of claim 1 wherein said isobutanol is formed in said hydrogenation.

12. The process of claim 1 wherein said isobutanol is added to said hydrogenation product before said distillation.

13. The process of claim 9 wherein the recycled isobutanol is dosed, whereby substantially all water is withdrawn at an upper side outlet.

* * * * *